United States Patent
Dai et al.

(10) Patent No.: US 10,961,491 B1
(45) Date of Patent: Mar. 30, 2021

(54) MAGNETIC BEAD-BASED NUCLEIC ACID EXTRACTION APPARATUS AND USE METHOD

(71) Applicant: SANSURE BIOTECH INC., Changsha (CN)

(72) Inventors: Lizhong Dai, Changsha (CN); Xu Fan, Changsha (CN); Ling Wu, Changsha (CN); Long Peng, Changsha (CN); Guo Fu, Changsha (CN)

(73) Assignee: SANSURE BIOTECH INC., Changsha (CN)

( * ) Notice: Subject to any disclaimer, the term of this patent is extended or adjusted under 35 U.S.C. 154(b) by 242 days.

(21) Appl. No.: 16/082,780

(22) PCT Filed: Dec. 26, 2016

(86) PCT No.: PCT/CN2016/112045
§ 371 (c)(1),
(2) Date: Oct. 24, 2018

(87) PCT Pub. No.: WO2017/152698
PCT Pub. Date: Sep. 14, 2017

(30) Foreign Application Priority Data

Mar. 8, 2016 (CN) .......................... 201610130289.8

(51) Int. Cl.
*C12M 1/42* (2006.01)
*C12N 15/10* (2006.01)

(52) U.S. Cl.
CPC .......... *C12M 1/42* (2013.01); *C12N 15/1013* (2013.01)

(58) Field of Classification Search
CPC .......................... C12M 1/42; C12M 15/1013
See application file for complete search history.

(56) References Cited

U.S. PATENT DOCUMENTS 3,356,346 A * 12/1967 Landsberger ....... B01F 13/0818
366/274
5,055,408 A * 10/1991 Higo .................. G01N 35/0098
141/130
(Continued)

FOREIGN PATENT DOCUMENTS

CN           1431290 A       7/2003
CN         101205246 A       6/2008
(Continued)

OTHER PUBLICATIONS

International Search Report and English Translation thereof, for International Application No. PCT/CN2016/112045, dated Mar. 9, 2017 (7 pages).
(Continued)

*Primary Examiner* — Brian R Gordon
(74) *Attorney, Agent, or Firm* — Kagan Binder, PLLC (57) ABSTRACT

The present application provides a magnetic bead-based nucleic acid extraction apparatus including a well plate, a magnetic attraction mechanism, a position moving mechanism, and an oscillation mechanism, a supporting base, and a fixing base disposed on the supporting base. The magnetic attraction mechanism includes a magnetic bar fixing base and a magnetic bar movably disposed on the magnetic bar fixing base. The position moving mechanism includes a ball screw and a driving motor; two ends of the ball screw are respectively connected to the magnetic bar fixing base and the driving motor. The oscillation mechanism includes a carrier and a main oscillation unit connected to the carrier. The main oscillation unit includes a motor spindle, an eccentric column, and a connecting base.

8 Claims, 5 Drawing Sheets

(56) References Cited

U.S. PATENT DOCUMENTS

| | | | | |
|---|---|---|---|---|
| 5,529,391 | A * | 6/1996 | Kindman | B01F 13/0818 366/145 |
| 5,558,839 | A * | 9/1996 | Matte | G01N 33/54333 422/552 |
| 5,779,907 | A * | 7/1998 | Yu | B01L 3/5085 210/695 |
| 6,368,561 | B1 * | 4/2002 | Rutishauser | B03C 1/30 422/527 |
| 6,645,431 | B2 * | 11/2003 | Astle | B01L 9/523 422/527 |
| 6,905,656 | B1 * | 6/2005 | Ladlow | B01F 13/0818 366/273 |
| 8,658,042 | B2 * | 2/2014 | Fasching | B03C 1/0332 210/695 |
| 8,920,751 | B2 * | 12/2014 | Barbee | G01N 35/0099 422/509 |
| 8,921,094 | B2 * | 12/2014 | Keller | C12Q 1/6806 435/287.2 |
| 9,140,634 | B1 * | 9/2015 | Knippschild | C12M 47/12 |
| 2002/0174878 | A1 * | 11/2002 | Nisson | B01L 9/523 134/1 |
| 2007/0077648 | A1 * | 4/2007 | Okamoto | B01L 7/52 435/303.1 |
| 2016/0289665 | A1 * | 10/2016 | Mao | C12N 15/1013 |
| 2017/0014787 | A1 * | 1/2017 | Douglas | B01F 15/00383 |
| 2017/0107508 | A1 * | 4/2017 | Higgins | C12N 15/1013 |

FOREIGN PATENT DOCUMENTS

| | | |
|---|---|---|
| CN | 102417902 A | 4/2012 |
| CN | 203238267 U | 10/2013 |
| CN | 103394410 A | 11/2013 |
| CN | 103697987 A | 7/2014 |
| CN | 103908945 A | 7/2014 |
| CN | 103923830 A | 7/2014 |
| CN | 104117429 A | 10/2014 |
| CN | 104371918 A | 5/2015 |
| CN | 204385205 U | 6/2015 |
| CN | 105543089 A | 5/2016 |
| CN | 205528702 U | 8/2016 |
| WO | 03090897 A1 | 6/2003 |

OTHER PUBLICATIONS

First Office Action arid English translation thereof, for Chinese Counterpart Patent Application No. 201610130239.8, dated Jun. 2, 2017 (17 pages).
Second Office Action and English translation thereof, for Chinese Counterpart Patent Application No. 201610130289.8, dated Feb. 13, 2018 (19 pages).
First Search Report of Chinese Counterpart CN201610130289.8 (2 pages).
Supplementary Search Report of Chinese Counterpart CN201610130289.8 (1 pages).

* cited by examiner

MAGNETIC BEAD-BASED NUCLEIC ACID EXTRACTION APPARATUS AND USE METHOD

The present application claims priority to Chinese Patent Application No. 201610130289.8, entitled "magnetic bead-based nucleic acid extraction apparatus and method of using the same", filed on Mar. 8, 2016, the entirety of which is incorporated herein by reference.

TECHNICAL FIELD

The present disclosure relates to the field of nucleic acid extraction apparatus, and more particularly to a magnetic bead-based nucleic acid extraction apparatus and a method of using the same.

BACKGROUND

With the popularization of genetic detection, personalized drug delivery, prenatal diagnosis, and the like, due to the pursuit of high-throughput and automation in all fields of the biological industry nowadays, the limitations of traditional DNA extraction methods are becoming more and more obvious. Since magnetic bead-based nucleic acid extraction can realize automatic extraction, large-scale operation, simple operation and short time-consuming, magnetic bead-based nucleic acid extraction has received more and more attention.

Generally, the extraction step of the magnetic bead-based nucleic acid extraction mainly comprises: (1) lysing; (2) binding; (3) washing; (4) separating. Specifically, the cell or tissue releases the DNA/RNA under the action of the lysate, and surface-modified superparamagnetic silica magnetic nanobeads specifically bind to the released DNA/RNA to form a nucleic acid-magnetic bead complex. A washing liquid is added to the nucleic acid-magnetic bead complex to wash away impurities such as non-specifically adsorbed proteins and the like, and the magnetic beads are separated and enriched, under a condition of magnetic field, from the nucleic acid-magnetic bead complex from which the impurities have been removed, and finally the nucleic acid to be extracted is obtained. During the nucleic acid extraction, homogeneous blending is required in all steps of lysing, washing and separating, so that the apparatus for nucleic acid extraction needs to have an oscillating function.

At present, there are mainly two methods for separating magnetic beads from a sample liquid, one of which is to use the combination of a rod magnet and a disposable outer casing to complete the collection of the magnetic beads. After the magnetic beads have been collected, they are transferred from one reagent into another reagent row by row, thereby completing the extraction of nucleic acids, the other method is to adsorb the magnetic particles in each well of the deep-well plate to a sidewall or a bottom row by row by a magnetic separation device, and inject or transfer a reagent by a pipetting robot arm to complete the treatment of different reagents, and then complete the process of nucleic acid extraction from one sample in a same well.

In the above two methods, the magnetic beads are readily taken away when a waste liquid is removed as the magnetic beads are adsorbed, thereby causing poor controllability of magnetic separation. The magnetic adsorption should be completed row by row, and the sample loading, pipetting, sample homogeneous blending, homogeneous blending in washing, homogeneous blending in separating are not synchronized with the magnetic adsorption, and is completed by transferring to an oscillator by using an plate gripper, thus having a poor time coordination and a high cost.

SUMMARY

The present disclosure provides a magnetic bead-based nucleic acid extraction apparatus and method, in order to solve the problem of poor time coordination caused by row-by-row moving operation required for the nucleic acid extraction apparatus for the completion of magnetic adsorption.

In a first aspect, the present disclosure provides a magnetic bead-based nucleic acid extraction apparatus comprising a deep-well plate, a magnetic attraction mechanism, a position moving mechanism, and an oscillation mechanism; wherein
the magnetic attraction mechanism comprises a magnetic bar fixing base and a magnetic bar movably disposed on the magnetic bar fixing base;
the position moving mechanism comprises a ball screw and a driving motor, two ends of the ball screw being connected to the magnetic bar fixing base and the driving motor, respectively;
the oscillation mechanism comprises a carrier and a main oscillation unit connected to the carrier;
the magnetic bar fixing base, the ball screw, and the driving motor are all located inside the carrier; and
the deep-well plate is detachably disposed on an upper surface of the carrier.

In conjunction with the first aspect, in a first possible implementation of the first aspect, the magnetic bead-based nucleic acid extraction apparatus further comprises a supporting base and a fixing base disposed on the supporting base, the main oscillation unit passes through the supporting base, and the driving motor is disposed on the fixing base.

In conjunction with the first aspect, in a second possible implementation of the first aspect, the magnetic bead-based nucleic acid extraction apparatus further comprises guide rails, four guide rails being provided, and evenly disposed on the fixing base.

In conjunction with the first aspect, in a third possible implementation of the first aspect, the main oscillation unit comprises a motor spindle, an eccentric column, and a connecting base, wherein the two ends of the eccentric column are respectively connected to the motor spindle and the connecting base, and the connecting base is connected to a bottom of the carrier.

In conjunction with the first aspect, in a fourth possible implementation of the first aspect, the main oscillation unit further comprises a photoelectric sensor and a photoelectric post disposed on the motor spindle, the position of the photoelectric sensor being corresponding to the position of the photoelectric post.

In conjunction with the first aspect, in a fifth possible implementation of the first aspect, an upper limit photoelectricity and a lower limit photoelectricity are provided at a vertical side of the carrier, and both are located inside the carrier, wherein the upper limit photoelectricity is near a top end of the carrier, and the lower limit photoelectricity is flush with a top of the driving motor.

In conjunction with the first aspect, in a sixth possible implementation of the first aspect, the magnetic bar fixing base is further provided with a photoelectric shield, and the photoelectric shield is used in conjunction with the upper limit photoelectricity.

In conjunction with the first aspect, in a seventh possible implementation of the first aspect, the deep-well plate is square and is regularly provided with a reaction tube, and four magnetic bars are evenly and equidistantly distributed around the reaction tube.

In conjunction with the first aspect, in an eighth possible implementation of the first aspect, the relationship between the reaction tube and the magnetic bar is: $M=N+X+Y+1$, wherein, M is the number of the magnetic bar; N is the number of the reaction tube; X is the number of rows of the reaction tube; and Y is the number of columns of the reaction tube.

In a second aspect, the present disclosure further provides a method of using a magnetic bead-based nucleic acid extraction apparatus, comprising:

S01: setting a test procedure;

S02: adding a lysis solution and a sample into a deep-well plate, activating the main oscillation unit, and oscillating the carrier and homogeneously blending the lysis solution and the sample according to a set time;

S03: after the completion of homogeneous blending, bringing the carrier back to initial position and ending the oscillating;

S04: after the completion of oscillation, adding the magnetic bead into the deep-well plate for reaction and oscillation;

S05: after the completion of reaction, stopping the oscillation, and rising the magnetic bar fixing base under the control of the driving motor, so that the magnetic bar reaches between the reaction tubes of the deep-well plate for magnetic bead adsorption, and a rising height of the magnetic bar may be freely adjusted according to a level of liquid;

S06: declining the magnetic bar fixing base under the control of the driving motor, so that the magnetic bead absorbed onto a wall of the reaction tube is enriched to a bottom of the reaction tube;

S07: removing a waste liquid, and bringing the magnetic bar fixing base back to initial position under the control of the driving motor;

S08: adding other reagent into the reaction tube of the deep-well plate, oscillating and homogeneously blending;

S09: after the completion of homogeneous blending, adding an organic solution or an inorganic solution, oscillating and homogeneously blending;

S10: after the completion of homogeneous blending, controlling the magnetic bar fixing base to rise, so that the magnetic bead is enriched to a layer of organic solution or inorganic solution in the reagent, and removing a waste liquid, layer by layer, to obtain a magnetic bead-nucleic acid complex;

S11: after bringing the magnetic bar fixing base back to the initial position under the control of the driving motor, adding a reaction solution into the magnetic bead-nucleic acid complex, oscillating and homogeneously blending to obtain the magnetic bead and the nucleic acid;

S12: after the completion of homogeneous blending, controlling the magnetic bar fixing base to rise, so that the bead is enriched to a bottom of the reagent, and transferring the nucleic acid to complete the nucleic acid extraction.

The present disclosure provides a magnetic bead-based nucleic acid extraction apparatus comprising a deep-well plate, a magnetic attraction mechanism, a position moving mechanism, and an oscillation mechanism; wherein the magnetic attraction mechanism comprises a magnetic bar fixing base and a magnetic bar movably disposed on the magnetic bar fixing base; the position moving mechanism comprises a ball screw and a driving motor, both ends of the ball screw being connected to the magnetic bar fixing base and the driving motor, respectively; the oscillation mechanism comprises a carrier and a main oscillation unit connected to the carrier; the magnetic bar fixing base, the ball screw, and the driving motor are all located inside the carrier; and the deep-well plate is detachably disposed on the upper surface of the carrier. The present disclosure provides a magnetic bead-based nucleic acid extraction apparatus with oscillating and homogeneous blending function by the carrier and the main oscillation unit of acid magnetic bead-based nucleic extraction apparatus, so that an enhanced blending effect and a faster blending speed of sample homogeneous blending, homogeneous blending in washing, homogeneous blending in separating etc., are made by oscillating; the position moving mechanism, by a up-and-down movement, is capable to drive the magnetic bar fixing base connected with the ball screw to move up and down precisely, so that the magnetic bars on the magnetic bar fixing base is located at different levels of the solution in the deep-well plate and provide magnetic attraction force for the magnetic bead, thereby facilitating operations, such as layer-by-layer removal of the waste liquid in the solution, and the like, and taking no magnetic bead away during the solution treatment; using the position moving mechanism in conjunction with the oscillating mechanism at different stages enables transferring of the solution, magnetic attraction, and oscillation to be performed at the same position, thereby avoiding transferring of a mechanical gripper between deep-well plates, and further reducing magnetic attraction time and cost.

BRIEF DESCRIPTION OF THE DRAWINGS

In order to more clearly illustrate the technical solution of the present disclosure, the drawings used in the embodiments will be briefly introduced below. It will be apparent to those skilled in the art that other drawings may be obtained from these drawings without inventive work.

TEXT DESCRIPTION

1—carrier, 2—magnetic bar fixing base, 3—deep-well plate, 4—guide rail, 5—ball screw, 6—driving motor, 7—fixing base. 8—main oscillation unit, 9—supporting base, 11—upper limit photoelectricity, 12—lower limit photoelectricity, 21—magnetic bar, 22—photoelectric shield, 31—reaction tube, 51—nut, 52—screw, 81—motor spindle, 82—eccentric column, 83—photoelectric sensor, 84—photoelectric post, 85—connecting base.

DESCRIPTION OF THE PREFERRED EMBODIMENTS

The present disclosure provides a magnetic bead-based nucleic acid extraction apparatus and a method using the same, solving the problem of poor time coordination caused by row-by-row moving operation required for the nucleic acid extraction apparatus for the completion of magnetic adsorption.

In order to make those skilled in the art better understand the technical solutions in the embodiments of the present disclosure, and to make the above objects, features and advantages of the embodiments of the present disclosure more obvious, the technical solutions in the embodiments of the present disclosure are further described in detail below with reference to the drawings.

Figure 1:
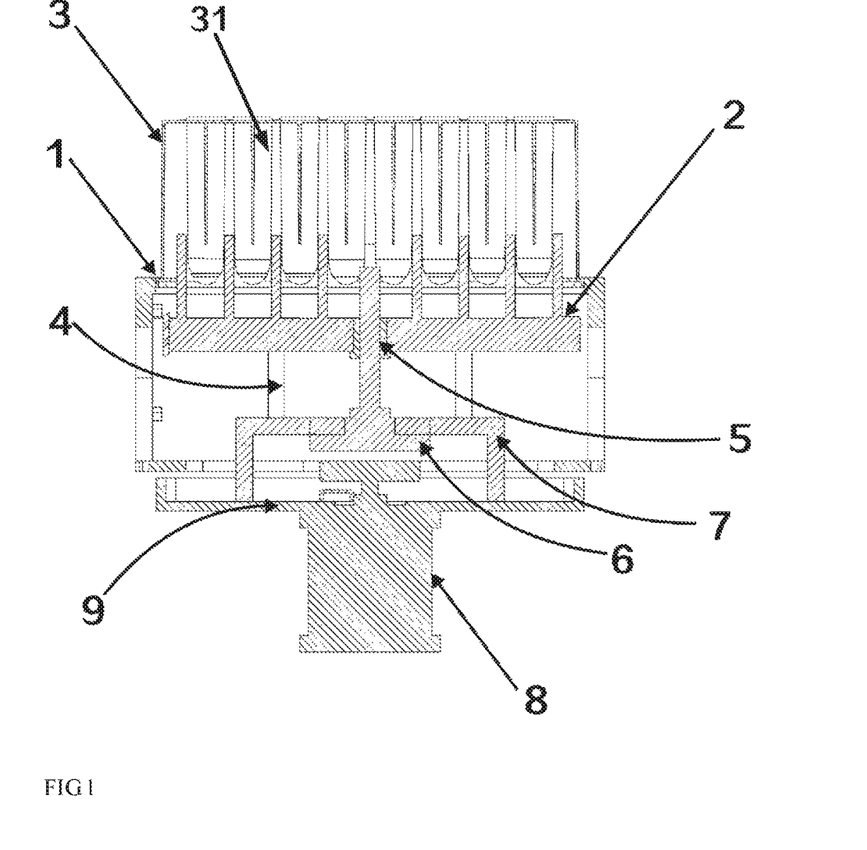
FIG. 1 is a structural diagram of a magnetic bead-based nucleic acid extraction apparatus provided in an embodiment of the present disclosure.

Reference is made to FIG. 1, a structural diagram of a magnetic bead-based nucleic acid extraction apparatus provided by the present disclosure is shown. The magnetic bead-based nucleic acid extraction apparatus provided by the present disclosure comprises a deep-well plate 3, a magnetic attraction mechanism, a position moving mechanism, and an oscillation mechanism.

Specifically, since different types of the deep-well plate 3, such as 48-deep-well plate, 96-deep-well plate, the PCR plate, are provided, the deep-well plate 3 is detachably disposed on an upper surface of a carrier 1 in order to facilitate replacement of different types of deep-well plate 3.

Figure 2:
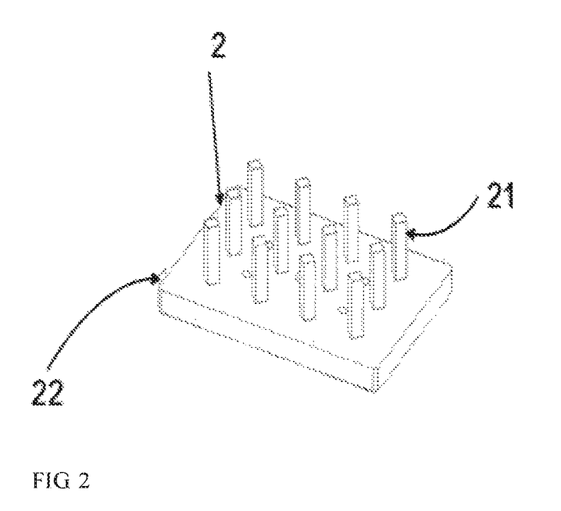
FIG. 2 is a structural diagram of a magnetic attraction mechanism in a magnetic bead-based nucleic acid extraction apparatus provided in an embodiment of the present disclosure.

The magnetic attraction mechanism comprises a magnetic bar fixing base 2 and a magnetic bar 21 movably disposed on the magnetic bar fixing base 2, referring to FIG. 2. Since a magnetic attraction force to a magnetic bead is supplied by the magnetic bar 21, the closer to a top end of the magnetic bar 21, the greater the magnetic attraction force is. During the magnetic attraction, four magnetic bars 21 are evenly and equidistantly distributed around a reaction tube 31 so that the magnetic bars 21 may provide a uniform magnetic force to the magnetic bead from different directions, and the attraction force to the magnetic bead does not attenuate as the magnetic bead is enriched, thereby achieving a strong adhesion of the magnetic bead on the reaction tube 31, and further facilitating the magnetic bar 21 to adsorb the magnetic bead or magnetic microbead in a liquid onto the reaction tube 31 during a shortest possible time.

In addition, for selection of the magnetic bar 21, the magnetic force from magnetic bar 21 should not be too strong, otherwise after the magnetic attraction is completed and the magnetic bar 21 are taken away from the magnetic microbead, residual magnetic force generated by the magnetic bar 21 will have an effect between microbeads, resulting in difficulty of homogeneous blending in subsequent reaction.

Regarding the magnetic bar 21 on the magnetic bar fixing base 2, different numbers and arrangements of the magnetic bar 21 may be arranged according to a shape of the deep-well plate 3 selected and the arrangement of the reaction tube 31 on the deep-well plate 3. In order to facilitate the arrangement of the magnetic bar 21, the magnetic bar 21 can be pluggably disposed on the magnetic bar fixing base 2.

Due to different shapes of the deep-well plate 3, the arrangement of the magnetic bars 21 around each reaction tube (31) is different. When the deep-well plate 3 is square, the number of the magnetic bars 21 has a certain relationship with the number of the reaction tubes 31. Where M is set as the number of the magnetic bars 21, N is set as the number of the reaction tubes 31, X is set as the number of rows of the reaction tubes 31, and Y is set as the number of columns of the reaction tubes 31, the quantitative relationship between the magnetic bars 21 and the reaction tubes 31 is $M=N+X+Y+1$, obtained from the four magnetic bars 21 being distributed evenly around each reaction tube 31. The above quantitative relationship is only applicable to the square deep-well plate 3, which the present disclosure is not limited to, and deep-well plate 3 in which the reaction tubes 31 are otherwise arranged are within the protection scope of the present disclosure.

Figure 3:
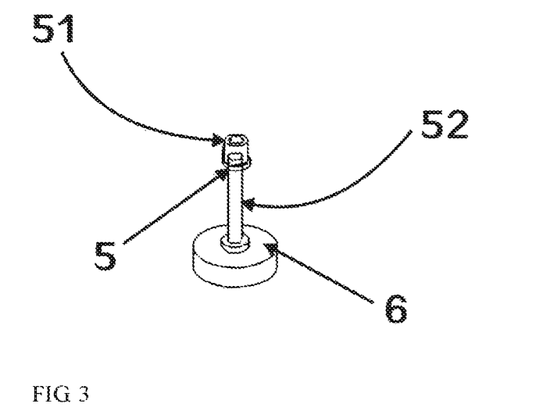
FIG. 3 is a structural diagram of a position moving mechanism in a magnetic bead-based nucleic acid extraction apparatus provided in an embodiment of the present disclosure.

The position moving mechanism comprises a ball screw 5 and a driving motor 6, both ends of the ball screw 5 being connected to the magnetic bar fixing base 2 and the driving motor 6, respectively, referring to FIG. 3 for details. The driving motor 6 powers for a up and down movement of the magnetic attraction mechanism. The ball screw 5 includes a nut 51 and a screw 52, the nut 51 and the screw 52 being connected in a mode of internal circulation or external circulation, such as built-in ball connection, matching internal and external thread rotation connection, and the like. Thus, the magnetic bar fixing base 2 may be moved in the up and down direction by the matching rotation of the nut 51 and the screw 52 under the driving of the driving motor 6, thereby realizing the use of the nucleic acid extraction in conjunction with the oscillation mechanism.

Figure 4:
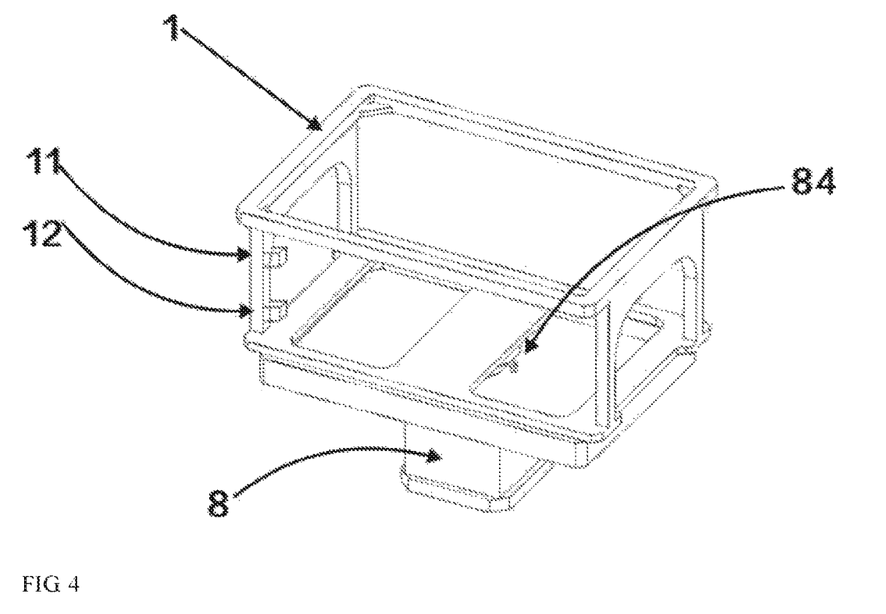
FIG. 4 is a structural diagram of an oscillation mechanism in a magnetic bead-based nucleic acid extraction apparatus provided in an embodiment of the present disclosure.

The oscillation mechanism comprises a carrier 1 and a main oscillation unit 8 connected to the carrier 1, referring to FIG. 4 for details. The carrier 1 can provide support for the placement of the deep-well plate 3 while protecting the magnetic bar fixing base 2, the ball screw 5 and the driving motor 6 from being damaged during an experiment or when the magnetic bead-based nucleic acid extraction device is idle. The magnetic bar fixing base 2, the ball screw 5 and the driving motor 6 are all located inside the carrier 1. The main oscillation unit 8 provides power for oscillation of the carrier 1 and the deep-well plate 3 to realize an oscillating function during nucleic acid extraction.

Further, the oscillation mechanism provided in an embodiment of the present disclosure further comprises an upper limit photoelectricity 11 and a lower limit photoelectricity 12 disposed at a vertical side of the carrier 1, and the upper limit photoelectricity 11 and the lower limit photoelectricity 12 are both located inside the carrier 1, wherein the upper limit photoelectricity 11 is near a top end of the carrier 1, and the lower limit photoelectricity 12 is flush with a top of the driving motor 6. The magnetic bar fixing base 2 is further provided with a photoelectric shield 22, the photoelectric shield 22 being used in conjunction with the upper limit photoelectricity 11. As the magnetic bar fixing base 2 drives the magnetic bars 21 to move upward, the driving motor 6 stops the electric driving when the upper limit photoelectricity 11 detects the photoelectric shield 22 on the magnetic bar fixing base 2, so that the magnetic bar fixing base 2 stops moving, thereby the magnetic bar 21 will not push the deep-well plate 3 out, which plays a protective role. Thus, using the photoelectric shield 22 in conjunction with the upper limit photoelectricity 11 can define an effective aperture spacing for the up and down movement of magnetic attraction mechanism. As the magnetic bar fixing base 2 drives the magnetic bars 21 to move downward, the driving motor 6 stops the electric driving when the lower limit photoelectricity 12 detects the photoelectric shield 22 on the magnetic bar fixing base 2, so that the magnetic bar fixing base 2 stops moving, and returns to initial position.

Therefore, the lower limit photoelectricity 12 is configured to determine whether the magnetic attraction mechanism is in the initial position. Using the upper limit photoelectricity 11, the lower limit photoelectricity 12 and the photoelectric shield 22 enables the magnetic bar fixing base 2 to be accurately stopped, thereby protecting the safety of the apparatus.

The magnetic bead-based nucleic acid extraction apparatus provided in the present disclosure further comprises a supporting base 9 through which the main oscillation unit 8 passes. The supporting base 9 is configured to support the entire apparatus of the present disclosure. Furthermore, a fixing base 7 is disposed on the supporting base 9, and the driving motor 6 is disposed on the fixing base 7. The fixing base 7 can provide a supporting force for the placement of the driving motor 6. Due to the supporting of the fixing base 7, the driving motor 6 and the main oscillation unit 8 do not affect each other in oscillating, and thus the magnetic adsorption and the oscillation do not affect each other.

The magnetic bead-based nucleic acid extraction apparatus provided by the present disclosure further comprises a guide rail 4 disposed on the fixing base 7. The magnetic attraction mechanism is driven by the driving motor 6 to move linearly along the guide rail 4 in the up and down direction under the matching rotation of the nut 51 and the screw 52, thereby providing the magnetic force to the deep-well plate 3. Further, there are four guide rails 4, which are all evenly disposed on the fixed base 7, so that the magnetic attraction mechanism can be moved up and down stably.

Figure 5:
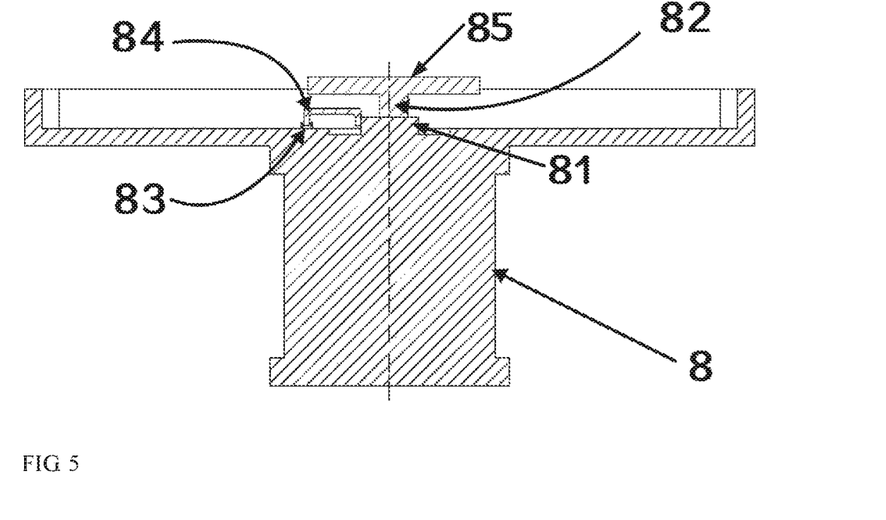
FIG. 5 is a structural diagram of a main oscillation unit in a magnetic bead-based nucleic acid extraction apparatus provided in an embodiment of the present disclosure.

Referring to FIG. 5, a structural diagram of a main oscillation unit 8 in the magnetic bead-based nucleic acid extraction apparatus provided by the present disclosure is shown. In the present disclosure, the main oscillation unit 8 comprises a motor spindle 81, an eccentric column 82, and a connecting base 85, wherein the two ends of the eccentric column 82 are respectively connected to the motor spindle 81 and the connecting base 85, the connecting base 85 is connected to a bottom of the carrier 1. Under the driving of electric power, the motor spindle 81 generates an eccentric rotation, so as to drive the eccentric column 82 to eccentrically move, thereby oscillating the carrier 1 connected to the connecting base 85, and realizing the oscillating function required for nucleic acid extraction.

Figure 6:
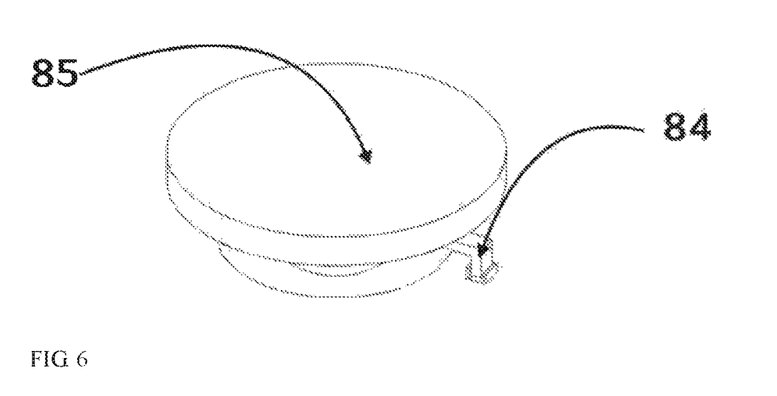
FIG. 6 is a structural diagram of a motor spindle in a magnetic bead-based nucleic acid extraction apparatus provided in an embodiment of the present disclosure.

Furthermore, the motor spindle 81 is provided with a photoelectric post 84, the main oscillation unit 8 is internally provided with a photoelectric sensor 83, and the photoelectric post 84 and the photoelectric sensor 83 are used cooperatively, referring to FIG. 6. When the motor spindle 81 rotates eccentrically, the photoelectric post 84 rotates in accordance with the eccentric rotation of the motor spindle 81, and the photoelectric sensor 83 inside the main oscillation unit 8 can detect the photoelectric post 84. When the photoelectric post 84 is located at a sensing point of the photoelectric sensor 83, the carrier 1 and the deep-well plate 3 return to its initial position, and the oscillation is finished. Therefore, using of the photoelectric post 84 in conjunction with the photoelectric sensor 83 can be used for positioning and counting of eccentric positions.

Since various solvents or substances need to be added into the reaction tube 31 at different extraction stages during nucleic acid extraction, the liquid level in the reaction tube 31 is different, thus a position of the magnetic bead in the reaction tube 31 is also different. In order to facilitate the magnetic bars 21 to attract the magnetic bead at different extraction stages, it is necessary to determine the position of the magnetic bar 21 between the reaction tubes 31. The magnetic bead-based nucleic acid extraction apparatus provided by the present disclosure can adjust an up and down moving distance of the magnetic bar fixing base 2 according to a height of the liquid level in the reaction tube 31, so that the magnetic bar 21 provides a maximum magnetic force for the magnetic bead. The process of adjusting the up and down moving distance of the magnetic bar fixing base 2 according to the height of the liquid level in the reaction tube 31 is as follows: the present apparatus detects the height of the liquid level in the reaction tube 31, and sends a detected value to the driving motor 6; and the driving motor 6 then controls the up-and-down movement of the magnetic bar fixing base 2. Since the ball screw 5 is consisted of the nut 51 and the screw 52, the moving distance of the magnetic bar fixing base 2 can be accurate to 0.1 mm, so that the magnetic bar 21 is raised above the liquid level or accurately moved at different levels of the layered liquid phase substance when the waste liquid is transferred. Therefore, it is advantageous to remove the waste liquid, layer by layer, shorten the magnetic separation time, and make magnetic adsorption completely without taking away the bead.

Figure 7:
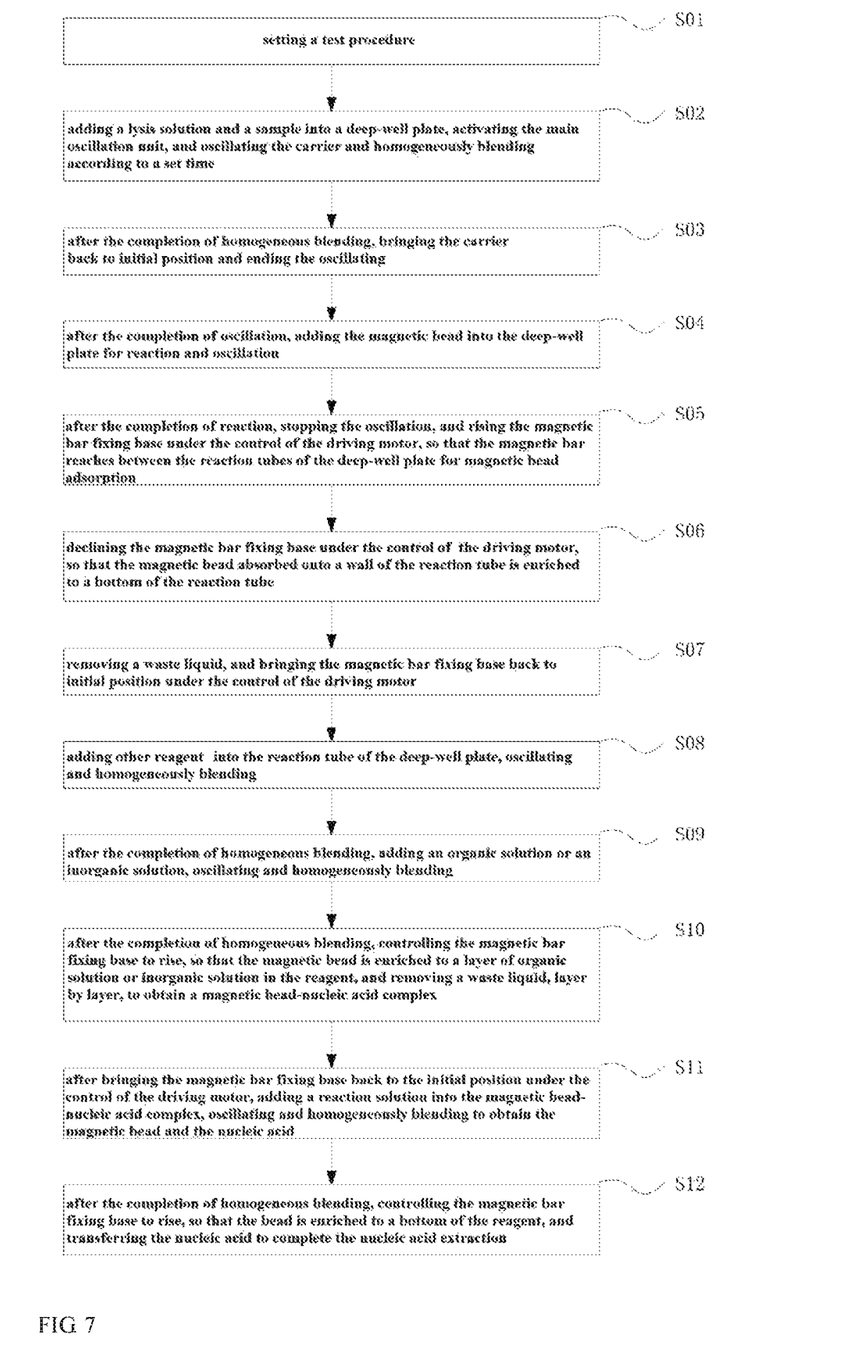
FIG. 7 is a flow chart of nucleic acid extraction using a magnetic bead-based nucleic acid extraction apparatus provided in an embodiment of the present disclosure.

An embodiment of the present disclosure provides a method for nucleic acid extraction using a magnetic bead-based nucleic acid extraction apparatus, and 96 samples can be prepared at one time by using the method, referring to FIG. 7, a flow chart of nucleic acid extraction using a magnetic bead-based nucleic acid extraction apparatus provided in an embodiment of the present disclosure is shown, the method of nucleic acid extraction comprises:

S01: setting a test procedure comprising test steps, oscillating time, and the like;

S02: adding a lysis solution and a sample into a deep-well plate using a disposable tip, activating the main oscillation unit, oscillating the carrier and the deep-well plate and homogeneously blending the lysis solution and the sample according to the set time;

S03: after the completion of homogeneous blending, locating the photoelectric post 84 on the motor spindle at a sensing point of the photoelectric sensor 83, so that the carrier and the deep-well plate return to the initial position, and the oscillation ends;

S04: after the completion of oscillation, adding the magnetic bead into the deep-well plate for reaction and oscillation according to the setting procedure;

S05: after the completion of reaction, stopping the oscillation, and rising the magnetic bar fixing base under the control of the driving motor, so that the magnetic bar reaches between the reaction tubes of the deep-well plate for magnetic bead adsorption, and a rising distance of the magnetic bar is determined by a liquid level in the reaction tube;

S06: declining the magnetic bar fixing base under the control of the driving motor, when the magnetic bead is absorbed on a side wall of the reaction tube, so that the magnetic bead absorbed to the reaction tube wall is enriched to a bottom of the reaction tube and formed into a mass.

S07: removing a waste liquid using a disposable tip to leave the bead in the reaction tube, and bringing the magnetic bar fixing base back to initial position under the control of the driving motor, while the magnetic bar no longer supplies a magnetic force to the magnetic bead in the reaction tube;

S08: adding other reagent into the reaction tube of the deep-well plate, oscillating and homogeneously blending;

S09: after the completion of homogeneous blending, adding an organic solution or an inorganic solution, oscillating and homogeneously blending again;

S10: after the completion of homogeneous blending, controlling the magnetic bar fixing base to rise, so that the magnetic bead is enriched into the layer of organic solution or inorganic solution in the reagent, and removing the waste liquid, layer by layer, using a disposable tip, to obtain a magnetic bead-nucleic acid complex;

S11: after bringing the magnetic bar fixing base back to the initial position under the control of the driving motor, adding a reaction solution into the magnetic bead-nucleic acid complex, oscillating and homogeneously blending to obtain the magnetic bead and the nucleic acid;

S12: after the completion of homogeneous blending, controlling the magnetic bar fixing base to rise, so that the bead is enriched to a bottom of the reagent, and transferring the nucleic acid using a disposable tip to complete the nucleic acid extraction.

In the above nucleic acid extraction process, the magnetic bead-based nucleic acid extraction apparatus provided in the embodiment of the present disclosure can realize the oscillation of the carrier 1 and the deep well plate 3 by the main oscillation unit 8, thereby realizing sample homogeneous blending, homogeneous blending in washing, homogeneous blending in separating with a faster blending speed and an enhanced homogeneous blending effect. In the process of the nucleic acid extraction, the magnetic attraction mechanism and the position moving mechanism collectively realize the adsorption of the magnetic bead at the stage where the magnetic attraction is required, without an inter-plate transferring between the deep-hole plates 3. Due to using the position moving mechanism in conjunction with the oscillating mechanism at different stages, transferring of the solution, magnetic attraction, and oscillation are all performed at the same position, thereby avoiding transferring of a mechanical gripper between deep-well plates, and further reducing magnetic attraction time and cost. In addition, using the upper limit photoelectricity 11, the lower limit photoelectricity 12 and the photoelectric shield 22 provided by the embodiment of the disclosure enables the magnetic bar fixing base 2 to be accurately stopped, thereby protecting the safety of the apparatus.

The embodiments of the present disclosure described above are not intended to limit the protection scope of the present disclosure. Any modifications, equivalent substitutions, improvements and the like made within the spirit and principle of the present disclosure are intended to be included within the protection scope of the present disclosure.

What is claimed is:

1. A magnetic bead-based nucleic acid extraction apparatus comprising a plate (3) with wells, a magnetic attraction mechanism, a position moving mechanism, an oscillation mechanism, a supporting base (9), and a fixing base (7) disposed on the supporting base (9); wherein the magnetic attraction mechanism comprises a magnetic bar fixing base (2) and at least one magnetic bar (21) movably disposed on the magnetic bar fixing base (2);

the position moving mechanism comprises a ball screw (5) and a driving motor (6), two ends of the ball screw (5) are respectively connected to the magnetic bar fixing base (2) and the driving motor (6);

the oscillation mechanism comprises a carrier (1) and a main oscillation unit (8) connected to the carrier (1);

the magnetic bar fixing base (2), the ball screw (5), and the driving motor (6) are all located inside the carrier (1);

the plate (3) with wells is detachably disposed on an upper surface of the carrier (1);

the main oscillation unit (8) passes through the supporting base (9);

the driving motor (6) is disposed on the fixing base (7); and the main oscillation unit (8) comprises a motor spindle (81), an eccentric column (82), and a connecting base (85), wherein two ends of the eccentric column (82) are respectively connected to the motor spindle (81) and the connecting base (85), and the connecting base (85) is connected to a bottom of the carrier (1).

2. The magnetic bead-based nucleic acid extraction apparatus according to claim 1, further comprises four guide rails (4) provided on and evenly disposed on the fixing base (7).

3. The magnetic bead-based nucleic acid extraction apparatus according to claim 1, wherein the main oscillation unit (8) further comprises a photoelectric sensor (83) and a photoelectric post (84) disposed on the motor spindle (81), the photoelectric post (84) rotates in accordance with an eccentric rotation of the motor spindle (81) and is detectable by the photoelectric sensor (83).

4. The magnetic bead-based nucleic acid extraction apparatus according to claim 1, wherein an upper limit photoelectricity (11) and a lower limit photoelectricity (12) are provided at a vertical side of the carrier (1), and both are located inside the carrier (1), wherein the upper limit photoelectricity (11) is closer to a top end of the carrier (1) relative to the lower limit photoelectricity (12) of the carrier (1); and the lower limit photoelectricity (12) is flush with a top of the driving motor (6).

5. The magnetic bead-based nucleic acid extraction apparatus according to claim 4, wherein the magnetic bar fixing base (2) is further provided with a photoelectric shield (22), and the photoelectric shield (22) is detectable by the upper limit photoelectricity (11).

6. The magnetic bead-based nucleic acid extraction apparatus according to claim 1, further comprising a reaction tube, and wherein the at least one magnetic bar (21) comprises a plurality of magnetic bars (21) that are evenly and equidistantly distributed around the reaction tube (31).

7. The magnetic bead-based nucleic acid extraction apparatus according to claim 1, further comprising a plurality of reaction tubes (31) and a plurality of magnetic bars (21), wherein each reaction tube (31) is disposed in a corresponding well of the plate (3) with wells, wherein the plate (3) with wells is cubic and wherein a relationship between the plurality of reaction tubes (31) and the plurality of magnetic bars (21) is: M=N+X+Y+1, wherein M is the number of the magnetic bars (21); N is the number of the reaction tubes (31); X is the number of rows of the reaction tubes (31); and Y is the number of columns of the reaction tubes (31).

8. A method of nucleic acid extraction using a magnetic bead-based nucleic acid extraction apparatus according to claim 1, wherein the magnetic bead-based nucleic acid extraction apparatus further comprises a plurality of reaction tubes (31) and a plurality of magnetic bars (21), wherein each reaction tube (31) is disposed in a corresponding well of the plate (3) with wells, wherein the method further comprises:

S01: adding a lysis solution and a sample into each reaction tube (31), activating the main oscillation unit, and oscillating the carrier from an initial motor spindle (81) position and homogeneously blending the lysis solution and the sample;

S02: after the completion of homogeneous blending, bringing the carrier back to the initial motor spindle (81) position and ending the oscillating, thereby obtaining a liquid comprising nucleic acid;

S03: after the completion of oscillation, adding magnetic beads into each reaction tube (31) for absorbing the nucleic acid in the liquid and oscillating;

S04: after the completion of absorbing the nucleic acid, stopping the oscillating, and raising the magnetic bar fixing base (2) from an initial magnetic bar fixing base (2) position under the control of the driving motor so that each magnetic bar (21) is positioned between adjacent reaction tubes to attract magnetic beads via magnetic attraction force toward an inside wall of each reaction tube;

S05: lowering the magnetic bar fixing base (2) under the control of the driving motor so that the magnetic beads attracted to the inside wall of each reaction tube concentrate toward a bottom of each reaction tube (31);

S06: removing a first waste liquid of S05 from each reaction tube (31), and bringing the magnetic bar fixing base (2) to the initial magnetic bar fixing base (2) position under the control of the driving motor;

S07: adding a washing reagent into each reaction tube, oscillating and homogeneously blending the washing reagent with the magnetic beads;

S08: after the completion of homogeneous blending of S07, adding an organic solution or an inorganic solution into each reaction tube (31), oscillating and homogeneously blending the organic solution or the inorganic solution with the magnetic beads;

S09: after the completion of homogeneous blending of S08, controlling the magnetic bar fixing base (2) to raise the magnetic bar fixing base (2) from the initial magnetic bar fixing base (2) position to attract magnetic beads via magnetic attraction force and concentrate the magnetic beads subjected to S08 into a layer of the organic solution or inorganic solution, and removing a second waste liquid layer by layer, thereby obtaining a magnetic bead-nucleic acid complex;

S10 bringing the magnetic bar fixing base (2) back to the initial magnetic bar fixing base (2) position under the control of the driving motor, followed by adding a reaction solution into each reaction tube (31) comprising the magnetic bead-nucleic acid complex, oscillating and homogeneously blending the reaction solution and the magnetic bead-nucleic acid complex, thereby obtaining separated magnetic beads and the nucleic acid;

S11 after the completion of homogeneous blending of S10, controlling the magnetic bar fixing base (2) to raise the magnetic bar fixing base (2) from the initial magnetic bar fixing base (2) position to attract magnetic beads via magnetic attraction force and concentrate the separated magnetic beads to the bottom of each reaction tube (31), and collecting a remaining solution comprising the nucleic acid of S10 from each reaction tube (31) to complete the nucleic acid extraction.

\* \* \* \* \*